United States Patent [19]

Phillipps et al.

[11] Patent Number: 4,537,196

[45] Date of Patent: Aug. 27, 1985

[54] SYSTEMS AND METHODS FOR PROCESSING PHYSIOLOGICAL SIGNALS

[75] Inventors: Patrick G. Phillipps, Wayland; Jeffrey Schenkel, Norwood, both of Mass.

[73] Assignee: American Home Products Corporation (Del.), New York, N.Y.

[21] Appl. No.: 333,088

[22] Filed: Dec. 21, 1981

[51] Int. Cl.³ .............................................. A61B 5/00
[52] U.S. Cl. ................................................... 128/630
[58] Field of Search .............. 128/630, 901, 902, 668, 128/687, 697, 702, 704, 706, 708; 435/415, 417; 307/516, 523, 525, 526, 527, 543, 529, 603; 333/139, 144, 152, 1

[56] References Cited

U.S. PATENT DOCUMENTS

| | | | |
|---|---|---|---|
| 3,174,478 | 3/1965 | Kahn | 128/706 |
| 3,482,190 | 12/1969 | Brenin | 333/139 |
| 3,569,852 | 3/1971 | Berkovits | 128/696 |
| 3,590,811 | 7/1971 | Harris | 128/708 |
| 3,965,339 | 6/1976 | Mount et al. | 364/417 |
| 4,064,537 | 12/1977 | Ota et al. | 307/543 |
| 4,161,945 | 7/1979 | Grossman | 128/901 |
| 4,243,045 | 1/1981 | Maas | 128/901 |
| 4,379,460 | 4/1983 | Judell | 128/671 |

OTHER PUBLICATIONS

Plumb et al., "IEEE Transactions on Biomedical Engineering, vol. 11, #4, Oct. 1964, pp. 157-159.

Primary Examiner—William E. Kamm
Attorney, Agent, or Firm—Edward M. Blocker

[57] ABSTRACT

For suppressing cardiovascular artifact present in a respiration signal, a cardiovascular artifact filter suppresses artifacts in response to an output signal generated by a cardiotachometer. The output signal is proportional to the fundamental frequency of the cardiovascular artifact. Recurrence of respiration is determined by coupling the filter to a threshold detector. A minimum threshold level proportional to the maximum amplitude of the artifact is supplied to the detector for minimizing the false indication of respiration recurrence due to presence of an artifact in the respiration signal.

13 Claims, 11 Drawing Figures

SYSTEMS AND METHODS FOR PROCESSING PHYSIOLOGICAL SIGNALS

THE BACKGROUND OF THE INVENTION

The present invention relates to physiological signal processing systems and methods.

Physiological functions typically are monitored by producing signals intended to represent these functions and processing such signals to extract useful data concerning the functions. Non-invasive monitoring techniques for acquiring such signals often provide a reduced risk of infection as compared to techniques which involve acquiring a signal directly from the bodily organ whose function is to be monitored. It is, however, difficult to avoid unintentionally receiving interferring components in such signals due to the functioning of adjacent organs, especially where non-invasive monitoring is undertaken.

For example, the monitoring of respiration by impedance pneumography involves the detection of relatively small changes in transthoracic impedance, which are occasioned both by the expansion and contraction of the lungs and by cardiovascular activity. Typically, a respiration event is detected when the respiration signal crosses a fixed threshold level, which may be adjustable by the user. If the threshold level is set too low, cardiovascular artifact can trigger the detection of a respiration event when in fact no respiration has occurred; apnea, therefore, can go undetected, with potentially severe consequences to the patient. If the threshold level is set too high, normally shallow breathing can go undetected, resulting in a false apnea alarm.

One approach to the solution of these problems assumes that the respiration signal will fall predominately in a range of frequencies below an arbitrarily selected frequency and that the cardiac components will fall predominately above that frequency. Accordingly, the respiration signal is processed by a low pass filter having a fixed cutoff frequency in order to suppress cardiovascular artifact in the respiratory signal. However, both respiration and heart rate can vary widely so that the foregoing assumption can lead to a disproportionately large cardiovascular artifact component in the respiration signal, with the possibility that a true apnea may be missed while the monitor counts artifact as respiration.

Another approach to these problems assumes that cardiovascular artifact will always be less than a certain percentage of the respriration signal. Accordingly, the threshold level is adjusted to a predetermined percentage of the last peak value of the respiration signal. However, large transients which will appear from time to time in the signal will cause an abrupt increase in the threshold level. Typically, the threshold level will be stored in a capacitor which will bleed charge to ground through a resistor to permit the threshold level to adjust downwardly when the peak value of the signal is decreasing. Due to the possibility of large transient pulses, a relatively short time constant must be selected, or false apnea detection may occur. This, however, creates a new problem; namely, the threshold level may fall off so rapidly that cardiovascular artifact may be detected as a respiration event, so that true apnea is missed.

In a modification of the foregoing method, it is assumed that when the detected respiration rate is the same as the heart rate, cardiovascular artifact is being detected by the respiration monitor. Accordingly, the threshold level is abruptly increased by an arbitrary amount when this occurs in an attempt to avoid counting cardiovascular artifact as a respiration event. This likewise requires that the threshold decrease rapidly thereafter so that true respiration can be detected and false apnea avoided. Once again, cardiovascular artifact can be counted as respiration and true apnea can be missed.

SUMMARY OF THE INVENTION

In accordance with one aspect of the present invention, a system is provided for detecting the recurrence of a periodic physiological function. The system comprises an input terminal for receiving a physiological signal representing the function, the physiological signal having periodic artifact. Means are coupled with the input terminal to receive the physiological signal, for producing a minimum threshold level from the physiological signal. Filtering means are coupled with the input terminal to receive the physiological signal for suppressing the periodic artifact in the physiological signal to produce a filtered signal therefrom. Threshold crossing detecting means are provided for producing a recurrence signal representative of the recurrence of the physiological function in response at least in part to the filtered signal exceeding a threshold level; the threshold crossing detecting means being coupled to sense the minimum threshold level and operative to maintain the threshold level equal to or in excess of the minimum threshold level. Accordingly, the possibility of false triggering due to the artifact is substantially reduced in comparison to the prior art by clamping the threshold level at or above a minimum level derived from the unfiltered physiological signal, while permitting the detection of the desired physiological function only when the filtered signal crosses the thus clamped threshold level, making it substantially more difficult for the artifact to trigger the detection of the recurrence of the physiological function.

In accordance with another embodiment of the present invention, a system is provided for detecting a patient's respiration. An input terminal is provided for receiving a respiration signal representing changes in the patient's thoracic volume. Cardiotachometer means are provided for producing a heart rate signal proportional to the patient's heart rate. Filtering means have an input coupled to the input terminal to receive the respiration signal, the filtering means being coupled to the cardiotachometer means to receive the heart rate signal produced by the cardiotachometer means. The filtering means are operative to provide a filtered respiration signal by suppressing frequency components of the respiration signal at the heart rate and harmonics thereof under the control of the heart rate signal. Threshold crossing detecting means have an input terminal coupled to receive the filtered respiration signal provided by the filtering means. The threshold crossing detecting means are provided for producing a respiration event signal when the filtered respiration signal exceeds a threshold signal level. The system is thus enabled to suppress cardiovascular artifact dispite changes in the heart rate, which might otherwise render conventional systems inadequate for this purpose.

In accordance with a further aspect of the present invention, a system is provided for suppressing periodic artifact in physiological signals. The system comprises an input terminal for receiving a physiological signal;

means for producing a frequency signal representative of the artifact frequency; and filtering means coupled with the input terminal to receive the physiological signal and with the producing means to receive the frequency signal, and responsive to the frequency signal for suppressing those components of the physiological signal at least at the fundamental frequency of the periodic artifact, the filtering means having an output terminal for providing the thus filtered physiological signal.

In accordance with a method of suppressing cardiovascular artifact in a respiration signal, the steps are provided of: obtaining from the patient a respiration signal representing changes in the volume of the patient's lungs, the respiration signal having artifact components resulting from cardiovascular activity; detecting the patient's heart rate and producing a signal representative thereof; and filtering the respiration signal by suppressing components thereof at the detected heart rate and at harmonics of the heart rate in response to the representative signal.

In accordance with another aspect of the present invention, a method is provided of detecting a patient's respiration, comprising the steps of: obtaining a respiration signal representing changes in the patient's thoracic volume, the respiration signal having cardiovascular artifact; producing a minimum theshold signal level from the respiration signal; filtering the cardiovascular artifact from the respiration signal to produce a filtered signal; and producing a recurrence signal at such times that the filtered signal exceeds a threshold signal level, while preventing the threshold signal level from falling below the minimum threshold signal level.

In a accordance with yet another aspect of the present invention, a system for detecting the recurrence of a periodic physiological function is provided. The system comprises an input terminal for receiving a physiological signal representing the function, the physiological signal having periodic artifact; means coupled with the input terminal to receive the physiological signal, for producing a threshold level from the physiological signal; filtering means coupled with the input terminal to receive the physiological signal for suppressing the periodic artifact in the physiological signal to produce a filtered signal therefrom; and threshold crossing detecting means for producing a recurrence signal representative of the recurrence of the physiological function in response at least in part to the filtered signal crossing the threshold level. By deriving the threshold level directly from the unfiltered physiological signal, while a recurrence signal is produced only when the filtered signal crosses the threshold level, the likelihood that the periodic artifact will result in the detection of the recurrence of the physiological function is substantially reduced.

In accordance with a still further aspect of the present invention, a threshold detector is provided, comprising: means for producing a threshold crossing signal in response at least in part to an input signal crossing an adjustable threshold level; and means for providing the adjustable threshold level to the producing means, comprising: storage means for storing the adjustable threshold level; comparing means for comparing the adjustable threshold level against a signal level proportional to at least a portion of the input signal to provide an update signal in response to a deviation of the adjustable threshold level from the proportional signal level toward a predetermined polarity; and updating means for modifying the adjustable threshold level in response to the update signal to oppose the deviation of the adjustable threshold level from the proportional signal level. The threshold detector so provided is relatively more flexible than prior art threshold detectors wherein the threshold is adjusted to a predetermined percentage of the most recent peak value of the signal applied to the threshold detector. For example, the occurrence of a large signal excursion, such as a brief transient, need not result in a correspondingly large increase in the threshold level. In a preferred embodiment of the present invention, the updating means is operative to modify the adjustable threshold level to a value porportional to the adjustable threshold level prior to the modification. In this manner, distortion of the threshold level by transient signals of short duration is avoided, while a true shift in the amplitude of the signal being detected leads to an appropriate adjustment of the threshold level.

In accordance with a method of detecting a breath event from a respiration signal representing changes in a patient's thoracic volume, the steps are provided of: establishing an initial respiration threshold level; producing an update signal in the event that the initial respiration threshold level deviates from a signal level proportional to at least a portion of the respiration signal towards a predetermined polarity; updating the initial respiration threshold level in response to the update signal to oppose the deviation of the initial respiration threshold level from the proportional signal level; and producing a breath event signal in response at least in part to at least a portion of the respiration signal exceeding in magnitude the updated respiration threshold level. Appropriate criteria for updating the initial respiration threshold level may be adopted which avoid the disadvantages of scaling the threshold level to the most recent peak of the respiration signal. For example, and in accordance with a preferred method of the present invention, the step of updating the initial respiration threshold level comprises altering said threshold level by an amount proportional to the initial respiration threshold level. By limiting the increase in the threshold to a predetermined proportion of the existing threshold level, the proportional increase can be selected such that no need exists to cause the threshold level thereafter to decay rapidly due to the possibility that large transients may undesirably increase the threshold level. The possibility that artifact may cause the detection of a breath event when in fact none has occurred, due to the rapid decrease in the threshold level before corrective action can be taken, may be minimized accordingly.

Further features and advantages of the invention will be apparent from the following detailed description of certain preferred embodiments, when taken in conjunction with accompanying drawings.

BRIEF DESCRIPTION OF THE DRAWINGS

The present invention is illustrated by way of example and not limitation in the figures of the accompanying drawings in which like numerals indicate similar elements and in which.

DESCRIPTION OF CERTAIN PREFERRED EMBODIMENTS

Figure 1:
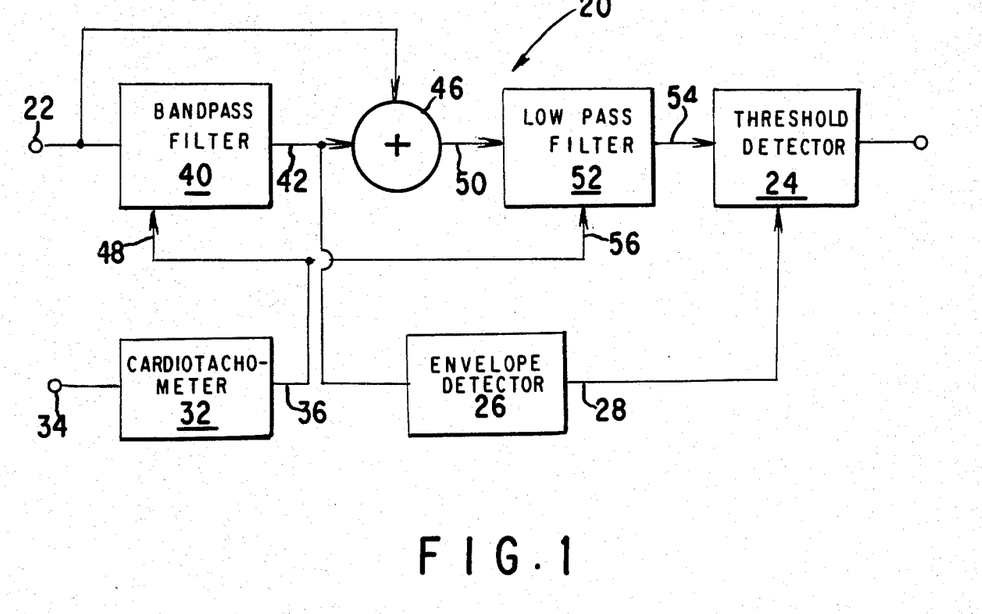
FIG. 1 is a block diagram of a system for detecting a patient's respiration from a respiration signal representing changes in the patient's thoracic volume, in accordance with one advantageous embodiment of the present invention.

With reference to FIG. 1, a system 20 for detecting a patient's respiration from a respiration signal representing changes in the patient's thoracic volume is illustrated. The respiration signal is received at an input terminal 22, from which the respiration signal is provided to a filtering system which suppresses frequency components of the respiration signal at the patient's heart rate and harmonics thereof in order to suppress cardiovascular artifact in the respiration signal. The thus filtered respiration signal is then provided to a threshold detector 24 which produces a respiration recurrence signal when the filtered respiration signal exceeds a threshold level derived from the prior history of the filtered respiration signal.

System 20 filters the respiration signal in accordance with a simplified approximation of a time averaging filtering scheme for suppressing components of the respiration signal at the patient's heart rate and harmonics thereof. Briefly, the time averaging filtering scheme in accordance with one embodiment of the present invention filters the respiration signal substantially in accordance with the relationship:

$$V_{fr}(t) = \int_0^T v_r(t)dt,$$

wherein $v_{fr}(t)$ represents the filtered respiration signal as it varies with time, t; $v_r(t)$ represents the respiration signal as it varies with time; t; and the interval 0 to T is variable under the control of a heart rate signal proportional to the patient's heart rate so that the interval 0 to T is substantially equal to the period of the fundamental frequency component of the heart rate. The heart rate signal is provided by a cardiotachometer 32 having an input terminal 34 which receives a pulse train representing individual beats of the patient's heart and provides the heart rate signal at an output terminal 36 which is a voltage proportional to the patient's heart rate. Accordingly, the filtering scheme of the present invention adapts its frequency characteristics with each heart beat in order to achieve highly selective suppression of cardiovascular artifact present in the respiration signal received at input terminal 22, despite beat-to-beat variations in the patient's heart rate.

The filtering scheme of FIG. 1 implements an approximation to a time averaging filter by cascading a notch filter with a low pass filter such that components of the respiration signal at the fundamental frequency of the cardiovascular artifact are first suppressed and then frequency components of the respiration signal having a frequency equal to or greater than the second harmonic of the patient's heart rate are suppressed. Since the respiration signal typically has a frequency lower than that of the cardiovascular artifact, system 20 achieves a substantial reduction in the amplitude of cardiovascular artifact components in the respiration signal as compared to that of components actually representing the patient's respiration. The notch or band-reject filter comprises a band pass filter 40 having an input connected to input terminal 22 to receive the respiration signal and an output terminal 42 connected to a summing input of a summing circuit 46. Band pass filter 40 is operative to pass frequency components of the respiration signal within a pass band including the fundamental frequency of the cardiovascular artifact as it varies. The output terminal 36 of cardiotachometer 32 is connected to a control terminal 48 of band pass filter 40 such that the heart rate signal automatically adjusts the pass band of filter 40 to track the fundamental frequency of the cardiovascular artifact. Band pass filter 40 is also operative to invert the frequency components of the respiration signal which it provides at its output terminal 42. A second summing terminal of summing circuit 46 is connected to input terminal 22, such that summing circuit 46 adds the respiration signal to the inverted components thereof provided at terminal 42 of filter 40. Accordingly, summing circuit 46 provides a signal at an output terminal 50 from which frequency components of the respiration signal within the pass band of filter 40 have been suppressed due to the cancelling effects of summing the respiration signal with the inverted components thereof within the pass band. The signal provided at terminal 50 is received by a low pass filter 52 at an input terminal thereof and provides the filtered respiration signal at an output terminal 54. Low pass filter 52 has a control terminal 56 connected to the output terminal 36 of cardiotachometer 32 to receive the heart rate signal which serves to control the frequency characteristics of low pass filter 52 such that those components of the respiration signal received at the input of low pass filter 52 having a frequency equal to or greater than the second harmonic of the heart rate are suppressed. Circuitry suitable for implementing band pass filter 40 and low pass filter 52 will be discussed in connection with FIG. 4.

The output terminal 54 of low pass filter 52 is connected to an input terminal of threshold detector 24 to provide the filtered respiration signal thereto. A second input terminal of threshold detector 24 is connected to an output terninal 28 of an envelope detector 26. An input terminal of envelope detector 26 is connected to output terminal 42 of bandpass filter 40 to receive a signal proportional to the fundamental frequency component of the cardiovascular artifact. Envelope detector 26 is operatve to provide a signal at its output terminal 28 which is proportional to the peak-to-peak excursion of this fundamental frequency component. As will be described in greater detail below, the signal at output terminal 28 establishes a minimum threshold level for threshold detector 24 which in effect places a lower limit on the threshold level derived by threshold detector 24 from the filtered respiration signal.

Figure 2:
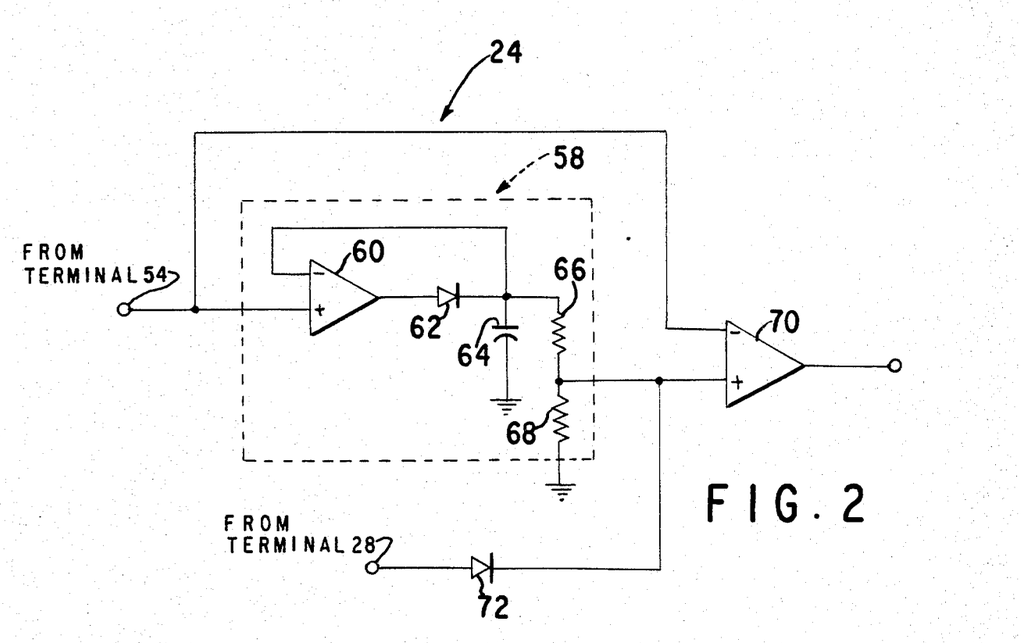
FIG. 2 is a schematic diagram of a threshold detector especially adapted for use in the embodiments of FIGS. 1, 3 and 5.

The operation of threshold detector 24 is now described with reference to FIG. 2 which shows a circuit suitable for implementing threshold detector 24. Threshold detector 24 includes a threshold establishing circuit 58 which includes an operational amplifier 60 having an inverting input terminal, a non-inverting input terminal and an output terminal. The non-inverting input terminal of amplifier 60 is connected to terminal 54 of low pass filter 52 to receive the filtered respiration signal. The output terminal of amplifier 60 is connected to the anode of a diode 62 and the inverting input terminal of amplifier 60 is connected to the cathode of diode 62 and to a first terminal of a storage capacitor 64. A second terminal of storage capacitor 64 is connected to ground. The first terminal of capacitor 64 is connected to a first terminal of a resistor 66 which has a second terminal connected to a first terminal of a resistor 68. A second terminal of resistor 68 is connected to ground.

Amplifier 60 serves to isolate the anode of diode 62 from terminal 54 and also serves to maintain the voltage level at the cathode of diode 62 substantially equal to the voltage level on terminal 54, since amplifier 60 will adjust its output voltage to maintain the voltage levels at its two input terminals substantially equal to one another. Capacitor 64 by virtue of its connection to the cathode of diode 62 will, therefore, charge to the peak positive voltage level appearing at terminal 54. Resistors 66 and 68 will bleed charge from capacitor 64 to permit the voltage thereacross to decay in the absence of a voltage at terminal 54 exceeding the voltage across capacitor 64.

An operational amplifier 70 has an inverting input terminal, a non-inverting input terminal and an output terminal. The non-inverting input terminal of amplifier 70 is connected to the second terminal of resistor 66 to receive a voltage therefrom proportional to the most recent peak value of the filtered respiration signal to establish a threshold level at the non-inverting input terminal of amplifier 70. The inverting input terminal of amplifier 70 is connected to terminal 54 to receive the filtered respiration signal therefrom. Accordingly, the voltage at the output terminal of amplifier 70 will abruptly change from a high voltage level to a low voltage level when the filtered respiration signal exceeds the threshold level established by circuit 58. This voltage transition constitutes a signal indicating the recurrence of respiration.

In order to minimize the likelihood that excursions of the filtered respiration signal from residual cardiovascular artifact will trigger the production of a recurrence signal at the output of amplifier 70, the threshold level at the non-inverting input terminal of amplifier 70 is prevented from falling below the minimum threshold level established by envelope detector 26. This is achieved by coupling output terminal 28 of envelope detector 26 to the non-inverting input terminal of amplifier 70 through a diode 72 having its anode connected to terminal 28 and its cathode connected to the non-inverting input terminal of amplifier 70. Diode 72, therefore, will become conductive when the minimum threshold level exceeds the threshold level established by circuit 58 by more than the voltage drop across diode 72 to feed current through resistor 68 and maintain the voltage level at the non-inverting input terminal of amplifier 70 at a voltage substantially equal to the minimum threshold level. As mentioned above, the minimum threshold signal is proportional to the fundamental frequency component of the cardiovascular artifact. Since the fundamental frequency component is proportional to the instantaneous magnitude of the cardiovascular artifact, the minimum threshold level produced by envelope detector 26 will be proportional to the maximum amplitude of the cardiovascular artifact. By scaling the minimum threshold level accordingly, the threshold level of threshold detector 24 is maintained at a level sufficiently high to avoid producing a respiration recurrence signal due to cardiovascular artifact.

Figure 3:
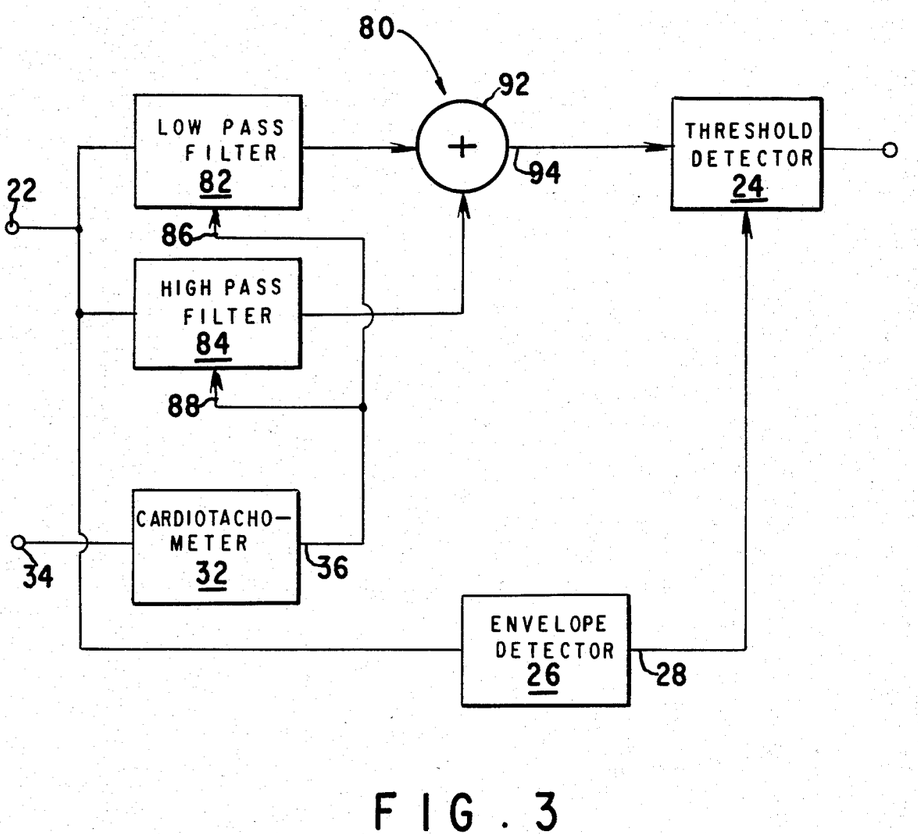
FIG. 3 is a block diagram of a further system for detecting a patient's respiration, in accordance with another advantageous embodiment of the present invention.

FIG. 3 illustrates a further system 80 for detecting a patient's respiration. In the system 80 of FIG. 4, the respiration signal received at input terminal 22 is provided simultaneously to the input terminals of a low pass filter 82 and a high pass filter 84. The frequency characteristics of filters 82 and 84 are adjusted by the application of a signal to their respective control terminals 86 and 88. Terminals 86 and 88 are connected to the output terminal 36 of cardiotachometer 32 to receive the heart rate signal therefrom. The heart rate signal adjusts the frequency characteristics of filters 82 and 84 such that components of the respiration signal at the fundamental frequency of the cardiovascular artifact as provided at the output terminal of filter 82 remain 180° out of phase with components of the respiration signal at the same frequency appearing at the output terminal of filter 84. The output terminals of filters 82 and 84 are connected to respective summing input terminals of a summing circuit 92. Accordingy, low pass filter 82, high pass filter 84 and summing circuit 92 act as a notch filter under the control of the heart rate signal to suppress components of the respiration signal at the fundamental frequency of the cardiovascular artifact as such filtered respiration signal is provided at an output terminal 94 of summing circuit 92.

The gain of high pass filter 84 is selected at a value lower than that of low pass filter 82 in order to attenuate components of the cardiovascular artifact at harmonic frequencies of the fundamental frequency thereof. Preferably, the gain of high pass filter 84 is selected at a value one-third of that of low pass filter 82. The filtered respiration signal provided at the output terminal 94 of summing circuit 92 is provided to threshold detector 24 in the same manner as the filtered respiration signal appearing on the output terminal 54 of low pass filter 42 of system 20, for the production of a recurrence signal by threshold detector 24 indicative of a respiration event.

Figure 4:
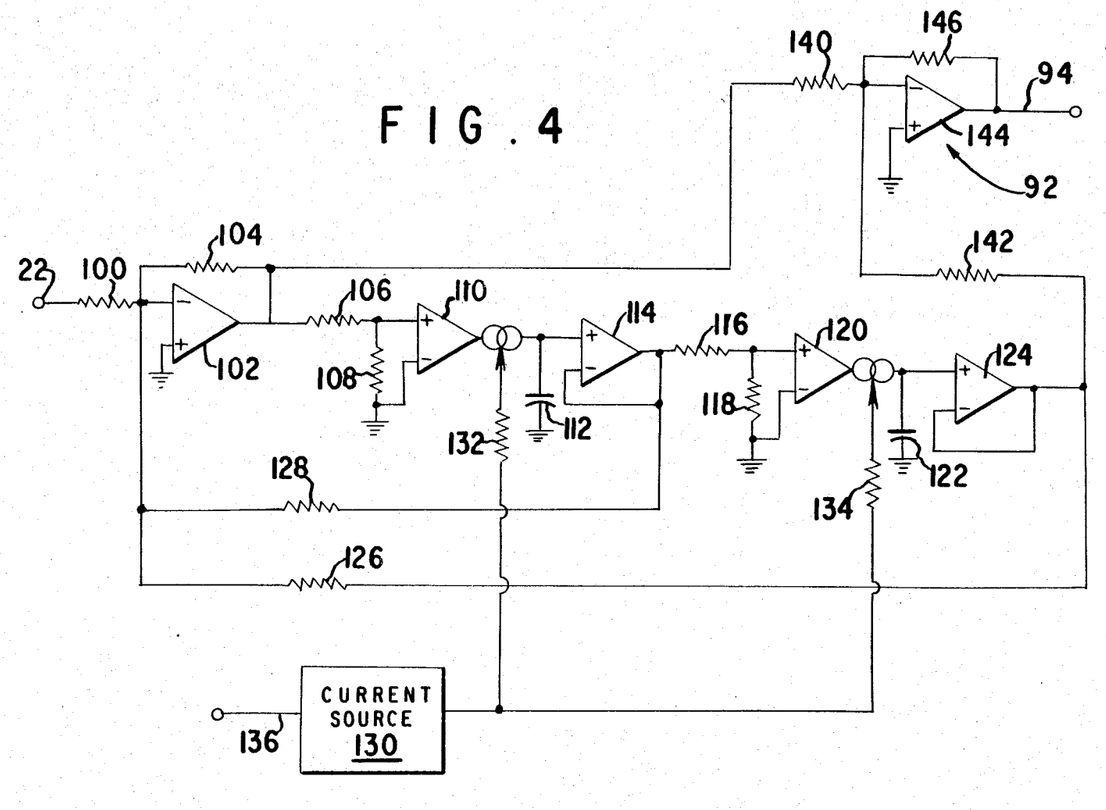
FIG. 4 is a schematic diagram, partially in block form, of a filter especially adapted for use in the present invention.

FIG. 4 illustrates a circuit adpated for use in the system of FIG. 3 for filtering cardiovascular artifact from a respiration signal. The circuit of FIG. 4 utilizes state variable filtering techniques to implement high pass, band pass and low pass filtering characteristics under the control of an external signal source. Accordingly, the band pass filter 40 and the low pass filter 52 of FIG. 1 may be implemented using state variable filtering techniques.

In the circuit of FIG. 4, input terminal 22 is coupled through a summing resistor 100 with the inverting input terminal of an operational amplifier 102. The non-inverting input terminal of amplifier 102 is connected to ground and the output of amplifier 102 is coupled to the inverting input terminal thereof through a feedback resistor 104. The output terminal of amplifier 102 produces an output voltage across a resistive voltage divider comprised of resistors 106 and 108 which are series connected such that a first terminal of resistor 106 is connected to the output terminal of amplifier 102, a second terminal of resistor 106 is connected to a first terminal of resistor 108 and a second terminal of resistor 108 is connected to ground. An operational transconductance amplifier 110 has a non-inverting input terminal connected to the second terminal of resistor 106 and an inverting input terminal connected to ground. Accordingly, a voltage proportional to the voltage appearing at the output terminal of amplifier 102 will appear across the non-inverting and inverting input terminals of amplifier 110. The output terminal of amplifier 110 is connected to a first terminal of an integrating capacitor 112 having a second terminal connected to ground. An operational amplifier 114 is connected as a voltage follower with its non-inverting input terminal connected to the first terminal of capacitor 112 so that the voltage appearing at the output terminal of amplifier 114 is substantially identical to that across capacitor 112. A second resistive voltage divider is comprised of resistors 116 and 118, wherein a first terminal of resistor 116 is connected to the output terminal of amplifier 114, a second terminal of resistor 116 is connected to a first terminal of resistor 118, and a second terminal of resistor 118 is connected to ground. A second operational transconductance amplifier 120 has its noninverting input terminal connected to the second terminal of resistor 116 and its inverting input terminal connected to ground, such that the voltage appearing across the non-inverting and inverting input terminal of amplifier 120 will be proportional to the voltage across capacitor 112. A second storage capacitor 122 has a first terminal connected to the output terminal of amplifier 120 and a second terminal connected to ground. An operational amplifier 124 is connected as a voltage follower with its noninverting input terminal connected to the first terminal of capacitor 122 and its output terminal coupled through a feedback resistor 126 to the inverting input terminal of amplifier 102. A feedback resistor 128 couples the output terminal of voltage follower 114 to the inverting input terminal of amplifier 102.

Control of the frequency characteristics of the circuit of FIG. 4 is achieved through the control of the current provided to the programming input terminals of operational transconductance amplifiers 110 and 120. The current is provided by a current source 130 having an output terminal coupled through resistors 132 and 134 respectively to the programmable input terminals of amplifier 110 and amplifier 120. The current provided by current source 130 is controlled in turn by a voltage provided at a control terminal 136 of current source 130. Terminal 136 is connected to the output terminal 36 of cardiotachometer 32 in FIG. 3 to receive the heart rate voltage, so that the latter controls the frequency characteristics of the circuit of FIG. 4.

The circuit of FIG. 4 provides high pass, band pass and low pass filtering of the respiration signal received at input terminal 22, respectively at the output terminals of amplifiers 102, 114 and 124. The component values are selected such that the output voltages of amplifiers 102 and 124 are 180° out of phase at the fundamental frequency of the the cardiovascular artifact, under the control of the heart rate signal received at terminal 136. Frequency control is achieved in that the heart rate voltage provided at terminal 136 will control the input current to the programmable input terminals of operational transconductance amplifiers 110 and 120, which in turn controls the transconductance of amplifiers 110 and 120 and thus the rate at which capacitors 112 and 122 charge. Since, as mentioned above, the output voltages of amplifiers 102 and 124 are 180° out of phase at the fundamental frequency of the cardiovascular artifact, these output voltages may be added to achieve rejection of those components of the respiration signal at the fundamental frequency of the cardiovascular artifact. Accordingly, the output terminal of amplifier 102 and the output terminal of amplifier 124 are connected to summing circuit 92 respectively at first terminals of summing resistors 140 and 142. The second terminal of each of resistors 140 and 142 is connected to the inverting input terminal of a summing amplifier 144. The non-inverting input terminal of amplifier 144 is connected to ground, and the output terminal of amplifier 144 is coupled to the inverting input terminal thereof through a feed back resistor 146. As mentioned above, the gain of the high pass filter is selected at a value less than the gain of the low pass filter in order to achieve rejection of the second and higher harmonics of the cardiovascular artifact in the respiration signal. This may be achieved by scaling the values of summing resistors 140 and 142 accordingly; for example, if it is desired to select the high pass gain as one-third of the low pass gain, the value of summing resistor 142 is selected as one-third the value of summing resistor 140.

Figure 5:
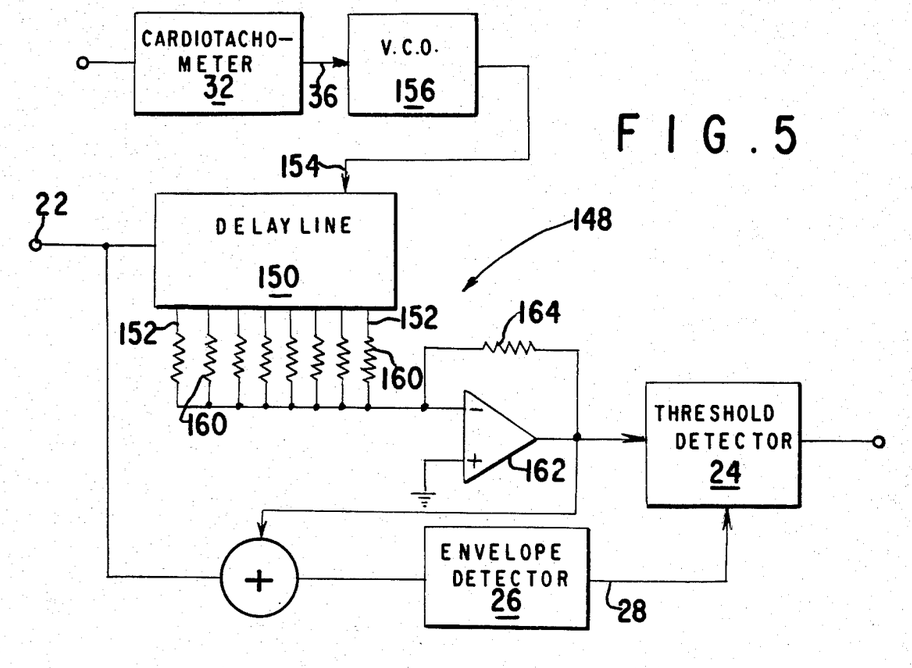
FIG. 5 is a block diagram of yet another system for detecting a patient's respiration, in accordance with further advantageous features of the present invention.

FIG. 5 illustrates still another system 148 for detecting a patient's respiration wherein filtering of the respiration signal to suppress cardiovascular artifact is achieved by approximating a time averaging filter as described hereinabove with circuitry operating in accordance with the relationship:

$$v_{fr} \propto \sum_{i=0}^{n} v_{ri}(n\Delta\tau)\Delta\tau$$

wherein $v_{fr}$ represents the filtered respiration signal; $v_{ri}(n\alpha\tau)$ represents the respiration signal delayed by a unique interval $(n\Delta\tau)$, where n equals 1,2 ... N. The foregoing relationship is realized in the system of FIG. 5 by applying the respiration signal received at terminal 22 to the input terminal of a tapped delay line 150 having n+1 output terminals each providing the respiration signal delayed by a unique interval $(n\Delta\tau)$, wherein $\Delta\tau$ is under the control of a clock signal received by delay line 150 at its clock input terminal 154. Cardiotachometer 32 has its output terminal 36 connected to the input terminal of a voltage control oscillator (VCO) 156 which in turn has its output terminal connected to clock input terminal 154. VCO 156 is operative under the control of the heart rate signal from cardiotachometer 32 to apply a pulse train to terminal 154 such that the oldest delayed respiration signal provided by delay line 150 is delayed with respect to the respiration signal at input terminal 22 by a time interval $N\Delta\tau$ which is substantially equal to the period between successive heart beats of the patient and therefore, equal to the period of the fundamental frequency component of the cardiovascular artifact.

Each of the output terminals 152 of delay line 150 is connected to a first terminal of a summing resistor 160, each of the summing resistors 160 having a second terminal connected to the inverting input terminal of an operational amplifier 162. The non-inverting input terminal of amplifier 162 is connected to ground and the output terminal of amplifier 162 is coupled to the inverting input terminal thereof through a feedback resistor 164. Accordingly, amplifier 162 provides a signal proportional to the sum of the delayed respiration signals provided at output terminals 152 of delay line 150, to thus provide the filtered respiration signal thereat.

Figure 6:
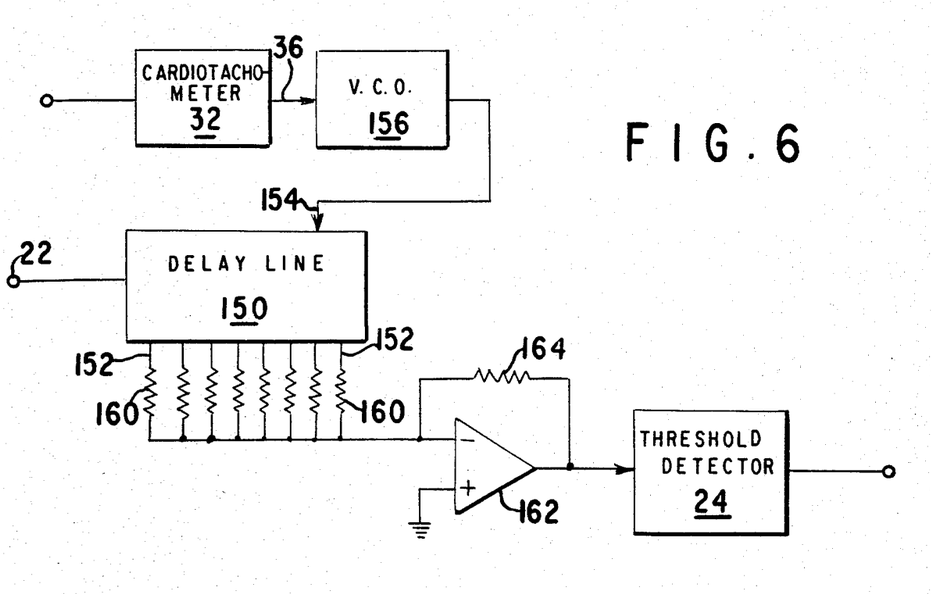
FIG. 6 is a block diagram of a system adapted for suppressing cardiovascular artifact in a respiration signal and detecting the recurrence of a respiration event.

The output terminal of amplifier 162 is connected to the input terminal of threshold detector 24 which provides the respiration recurrence signal at its output terminal as described hereinabove. Envelope detector 26 is operative as explained in connection with FIG. 1 to set a minimum threshold level of threshold detector 24, thus to minimize the likelihood that cardiovascular artifact will trigger the production of a respiration recurrence signal by threshold detector 24. However, the system of FIG. 5 may be implemented without setting a minimum threshold level for threshold detector 24, as shown in FIG. 6. Accordingly, envelope detector 26 is omitted from the system of FIG. 6 and the threshold detector 24 thereof would be modified to delete diode 72. It will be appreciated that the systems of FIGS. 1, 3, 5 and 6 may be readily adapted for detecting the recurrence of physiological functions other than respiration especially where the signal representing such a function carries a periodic artifact component.

Figure 7:
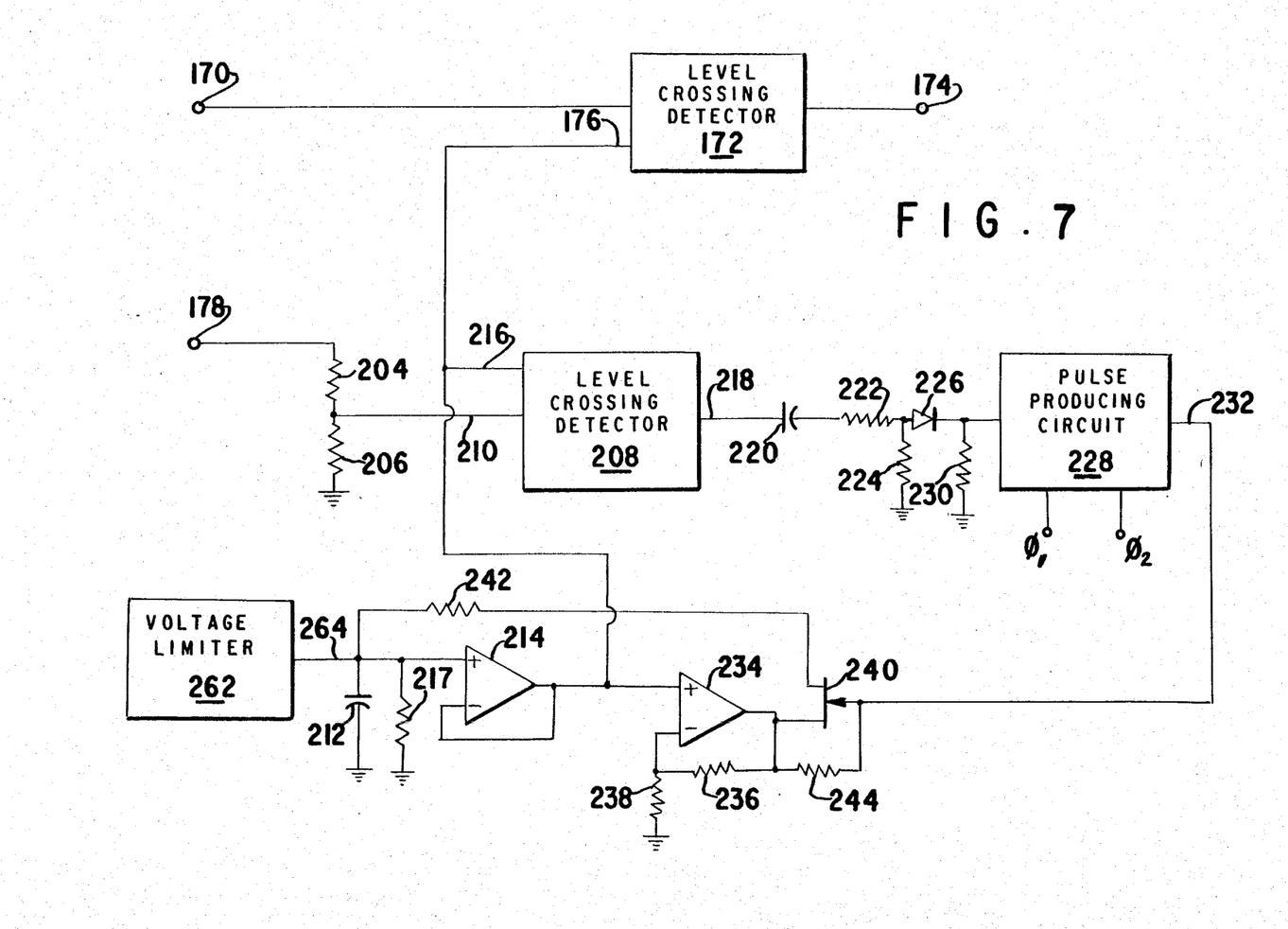
FIG. 7 is a block diagram, partially in schematic form, of a threshold detector in accordance with the present invention.

FIG. 7 illustrates a threshold detector adapted for use in the above-described systems. For example, the threshold detector of FIG. 7 may be incorporated in the above-described systems in place of the threshold detector 24 and with the elimination of envelope detector 26. It will be appreciated that the threshold detector of FIG. 7 is well adapted for detecting the recurrence of physiological functions other than respiration from a signal representing the function.

In the threshold detector of FIG. 7, an input signal, for example, the filtered respiration signal provided at the output terminal 54 of low pass filter 52 in the system 20 of FIG. 1, is received at an input terminal 170 of a level crossing detector 172 which produces a threshold crossing signal at an output terminal 174, for example, the respiration recurrence signal indicating that a respiration event has taken place. An adjustable threshold level is received by level crossing detector 172 at a threshold level input terminal 176. The threshold crossing signal is produced by the level crossing detector 174 as a response in part to the input signal received at terminal 170 crossing the adjustable threshold level provided at terminal 176, as described more fully below.

The adjustable threshold level is determined in the threshold detector of FIG. 7 by comparing the adjustable threshold level against a signal level proportional to a signal received at a second input terminal 178. For example, the signal received at terminal 178 may be the respiration signal received at terminal 22 of system 20 of FIG. 1. Based upon a comparison of the adjustable threshold level with the proportional signal level, the threshold detector provides an update signal in response to a deviation of the adjustable threshold level from the proportional signal level toward a predetermined polarity. For example, an update signal may be produced when the adjustable threshold level falls below the proportional signal level. The threshold detector of FIG. 7 responds to the update signal to oppose the deviation of the adjustable threshold level from the proportional signal level. Accordingly, the threshold detector of FIG. 7 is not constrained to utilize a threshold level proportional to the most recent peak value of the input signal, as is the threshold detector of FIG. 2, and may therefore avoid the problems associated therewith. In contrast to the threshold detector of FIG. 2, the threshold detector of FIG. 7 responds to an update signal to modify the adjustable threshold level to a value proportional to the adjustable threshold level prior to the modification. Accordingly, the presence of a large transient in the signal received at terminal 178 can only result in a modification of the adjustable threshold level based on the latter's pre-existing magnitude, thus to avoid distortion of the adjustable threshold level due to such a transient and where, for example, respiration is being monitored by the threshold detector of FIG. 7, false apnea due to a large increase in the adjustable threshold level will not occur. Likewise, the need to rapidly decay the threshold level to correct for such a large increase is avoided, and the likelihood of a consequent triggering of the threshold detector due to artifact in the signal being monitored is reduced.

Figure 8:
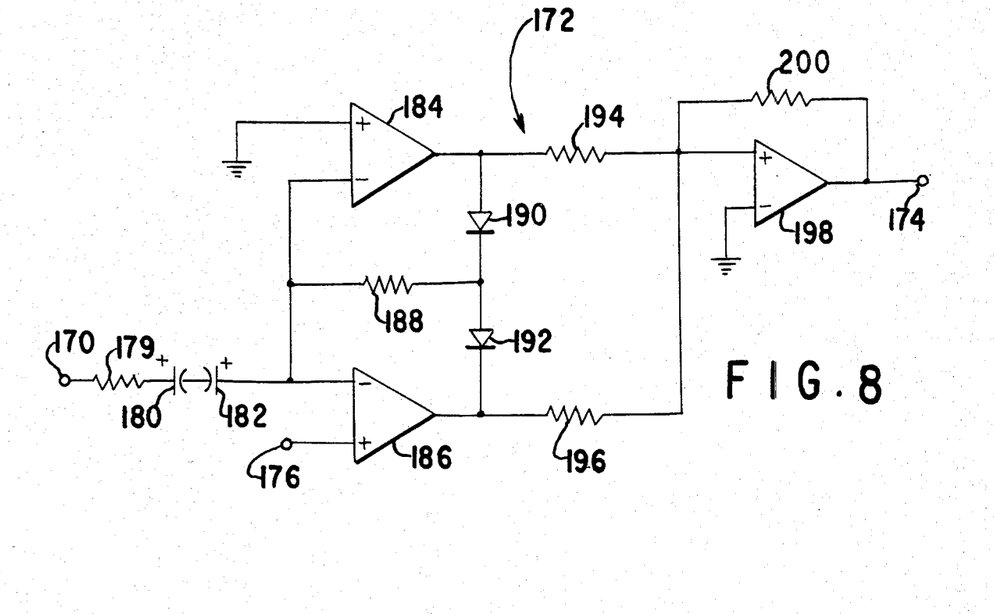
FIGS. 8 and 9 are schematic diagrams of level crossing detectors especially adapted for use in the threshold detector of FIG. 7.

The threshold detector of FIG. 7 will be explained in greater detail in connection with FIGS. 8–11. FIG. 8 is a schematic diagram of the level crossing detector 172 shown in block form in FIG. 7. The signal received at input terminal 170 of level crossing detector 172 is coupled through a current limiting resistor 179 and a pair of back-to-back capacitors 180 and 182 to the inverting input terminals of a pair of operational amplifiers 184 and 186. Capacitors 180 and 182 may be, for example, aluminum or tantalum capacitors. The non-inverting input terminal of operational amplifier 184 is connected to ground, while the non-inverting input terminal of operational amplifier 186 is connected to the threshold level input terminal 176. A first terminal of a current limiting resistor 188 is connected to the inverting input terminals of amplifiers 184 and 186. A first diode 190 has its anode connected to the output terminal of amplifier 184 and its cathode connected to a second terminal of resistor 188, while a second diode 192 has its anode connected to the second terminal of resistor 188 and its cathode connected to the output terminal of amplifier 186. A resistor 194 has a terminal connected to the output terminal of amplifier 184 and a resistor 196 has a terminal connected to the output terminal of amplifier 186. A second terminal of each of resistors 194 and 196 is connected to the non-inverting input terminal of an operational amplifier 198, which has its inverting input terminal connected to ground. The output terminal of amplifier 198 is coupled to its non-inverting input terminal through a feedback resistor 200. The output terminal of amplifier 198 is connected to the output terminal 174 of the level crossing detector 172.

In operation, the input signal received at terminal 170 is AC coupled to the inverting input terminals of amplifiers 184 and 186 which are operative to compare the AC coupled signal to the voltage level established at their respective non-inverting input terminals. Accordingly, so long as the AC coupled signal appearing at the inverting input terminal of amplifier 184 remains above ground, the voltage level at the output terminal of amplifier 184 will remain low and maintain diode 190 back biased, whereas so long as the AC coupled signal remains below the adjustable threshold level provided at terminal 176, the voltage appearing at the output terminal of amplifier 186 will remain high, thus maintaining diode 192 in a back biased condition. Resistors 194 and 196 are chosen to have substantially the same resistance so that so long as the voltage level of the AC coupled input signal remains between ground and the adjustable threshold level, the voltage appearing at the non-inverting input terminal of amplifier 198 will be an attenuated version of the output voltage at terminal 174. Due to the positive feedback provided by feedback resistor 200, which may be selected, for example, as twice the resistance of resistors 194 and 196, the extent voltage level at the output terminal of amplifier 198 will remain unchanged. However, should the AC coupled input voltage, for example, fall below ground, the output voltage of amplifier 184 will abruptly change to a high level which, due to the already high level of the output voltage of amplifier 186, will consequently raise the voltage level at the non-inverting input terminal of amplifier 198. On the other hand, should the voltage level of the AC coupled input signal exceed the adjustable threshold level, the output voltage of amplifier 186 will abruptly change to a low voltage level which, due to the already low voltage level at the output of amplifier 184, will pull the voltage level at the non-inverting input terminal of amplifier 198 to a low level. The effect of such voltage transitions on the output voltage of amplifier 198 will depend on the pre-existing voltage level thereof. That is, if said voltage level is high when the voltage level at its non-inverting input terminal is pulled low when the AC coupled input signal voltage exceeds the adjustable threshold level, the positive feedback through resistor 200 will be overcome and the output voltage of amplifier 198 will abruptly change to a low level, whereas if the AC coupled input voltage level should fall below ground, an extant high voltage level at the output terminal of amplifier 198 will remain unchanged. Conversely, if the voltage level at the output of amplifier 198 is low when the voltage level of the AC coupled input signal falls below ground, the output voltage of amplifier 198 will abruptly change to a high level, whereas should the voltage level of the AC coupled input signal exceed the adjustable threshold level, an existing low level voltage at the output terminal of amplifier 198 will remain unchanged. Diodes 190 and 192 together with current limiting resistor 188 serve to discharge capacitors 180 and 182 whenever the voltage level of the AC coupled input signal should either fall below ground or exceed the adjustable threshold level.

It is an important purpose of the remainder of the threshold detector of FIG. 7 to maintain the adjustable threshold level high enough to prevent the level crossing detector 172 from producing a respiration recurrence signal due to residual cardiovascular artifact in the filtered respiration signal. This is achieved by comparing the adjustable threshold level against a signal level proportional to the respiration signal and producing an update signal in response to a deviation of the adjustable threshold level from the proportional signal level toward a predetermined polarity, whereupon the adjustable threshold level is modified in response to the update signal to oppose the deviation of the adjustable threshold level from the proportional signal level. Since the adjustable threshold level is maintained about a value proportional to the unfiltered respiration signal, the adjustable threshold level is automatically raised to account for the presence of cardiovascular artifact in the unfiltered respiration signal, thus to minimize the likelihood that level crossing detector 172 will trigger due to cardiovascular artifact.

Figure 9:
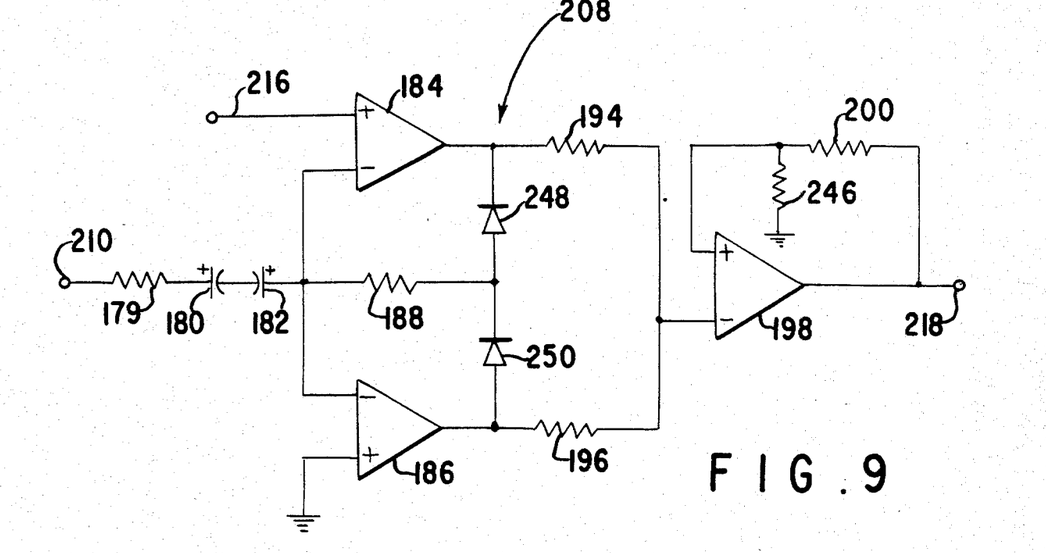

The second input terminal 178 may, for example, be connected to the input terminal 22 of the system of FIG. 1 to receive the unfiltered respiration signal. A resistor 204 has a first terminal connected to terminal 178 and a second terminal connected to a first terminal of a resistor 206. A second terminal of resistor 206 is connected to ground. Accordingly, a signal level proportional to the unfiltered respiration signal will be provided at the second terminal of resistor 204. A second level crossing detector 208 has a threshold input terminal 210 connected to the second terminal of resistor 204 to receive the proportional signal level therefrom. A threshold storage capacitor 212 which stores the adjustable level has a first terminal connected to the non-inverting input terminal of an operational amplifier 214 and a second terminal connected to ground. A bleeder resistor 217 is connected between the first terminal of capacitor 212 and ground. Amplifier 214 is connected in a voltage follower configuration and has its output terminal connected to an input terminal 216 of level crossing detector 208 and to the threshold level input terminal 176 of level crossing detector 172. Level crossing detector 208, which will be described in greater detail in connection with FIG. 9, is operative to provide a positive going pulse at an output terminal 218 when the adjustable threshold level stored in capacitor 212 falls below the magnitude of the AC component of the proportional signal level, after the AC component of the proportional signal level has fallen below ground without an intervening excursion of said AC component above the adjustable threshold level. The positive going output pulse provided at terminal 218 serves to indicate that an increase in the adjustable threshold level is warranted.

The first terminal of a capacitor 220 is connected to output terminal 218 and a second terminal of capacitor 220 is connected to a first terminal of a resistor 222. A second terminal of resistor 222 is connected to a first terminal of a resistor 224 having a second terminal connected to ground. Accordingly, the pulse appearing at terminal 218 is differentiated and attenuated as it appears at the second terminal of resistor 222. A diode 226 has its anode connected to the second terminal of resistor 222 and its cathode connected to an input terminal of a pulse producing circuit 228 and to the first terminal of a resistor 230. A second terminal of resistor 230 is connected to ground. Pulse producing circuit 228 is operative to provide pulses of predetermined duration at an output terminal 232 in response to the receipt of the differentiated update signal at its input terminal. The duration and frequency of the pulses provided at output terminal 232 is controlled by two clock signals received at clock inputs $\phi_1$ and $\phi_2$ of pulse producing circuit 228. As the input circuitry of pulse producing circuit 228, which will be explained more fully in connection with FIG. 10, is CMOS circuitry and thus has a very high input impedance, resistor 230 serves to bleed charge stored therein and blocked by diode 226 and the resistive voltage divider comprised of resistors 222 and 224 together with diode 226 serve to maintain the voltages received at the input terminal of pulse producing circuit 228 within the range of 0 to +5 volts.

An updating circuit includes an operational amplifier 234 having its non-inverting input terminal connected to the output terminal of amplifier 214 and its output terminal coupled through a feedback resistor 236 to its inverting input terminal which is coupled to ground through a resistor 238. Accordingly, amplifier 234 serves to amplify the adjustable threshold level and to provide the thus amplified threshold at its output terminal. The output terminal of amplifier 234 is connected to the drain of a field effect transitor 240 which has its source coupled to the first terminal of storage capacitor 212 through a charging resistor 242. Output terminal 232 of pulse producing circuit 228 is coupled to the gate of transistor 240 and through a resistor 244 to the output terminal of amplifier 234. Accordingly, a positive going pulse of sufficient magnitude at terminal 232 will turn on transistor 240 to permit capacitor 212 to charge through resistor 242, but since the duration of the positive going pulse at terminal 232 is limited to a predetermined period, the adjustable threshold level stored in capacitor 212 will only be modified at any one time by a value proportional to the adjustable threshold level prior to the modification, so that an update pulse resulting from a large transient voltage appearing at terminal 178 will not result in a large increase in the adjustable threshold level.

FIG. 9 is a schematic diagram of the level crossing detector 208 shown in block form in FIG. 7. Elements of the level crossing detector 208 corresponding to those in the level crossing detector 172 are designated by the same reference numerals. In the level crossing detector 208, the non-inverting input terminal of amplifier 186 is connected to ground and the non-inverting input terminal of amplifier 184 is connected to input terminal 216 to receive the adjustable threshold level from the output terminal of voltage follower 214, while the first terminal of resistor 179 is connected to threshold input terminal 210 to receive the proportional signal level. Accordingly, a high to low voltage transition at the output terminal of amplifier 184 will be triggered in the event that the adjustable voltage level received at terminal 216 falls below the AC component of the proportional signal level which is received by amplifier 184 at its inverting input terminal. In order to provide a positive going pulse upon a high to low transition at the output terminal of amplifier 184, amplifier 198 has its inverting input terminal connected to the second terminals of resistors 194 and 196, while positive feedback to the non-inverting input terminal of amplifier 198 is provided through a voltage divider comprised of feedback resistor 200 and a resistor 246 connected between the non-inverting input terminal of amplifier 198 and ground. Upon a high to low transition of the output voltage of amplifier 184, therefore, the inverting input terminal of amplifier 198 will be forced low and the output voltage thereof forced high. In the event that the output voltage of amplifier 198 had previously been low as a result of an excursion of the AC component of the proportional signal level below ground, a positive going pulse will be produced at output terminal 218 to trigger an update of the adjustable threshold level stored in capacitor 212. Due to the modification in the connections of the non-inverting input terminals of amplifiers 184 and 186, diodes 190 and 192 of level crossing detector 172 are replaced in level crossing detector 208 by diodes 248 and 250 which are connected such that the cathode of diode 248 is connected to the output terminal of amplifier 184 while its anode is connected to the second terminal of resistor 188, whereas the cathode of diode 250 is connected to the second terminal of resistor 188 while its anode is connected to the output of amplifier 186.

Figure 10:
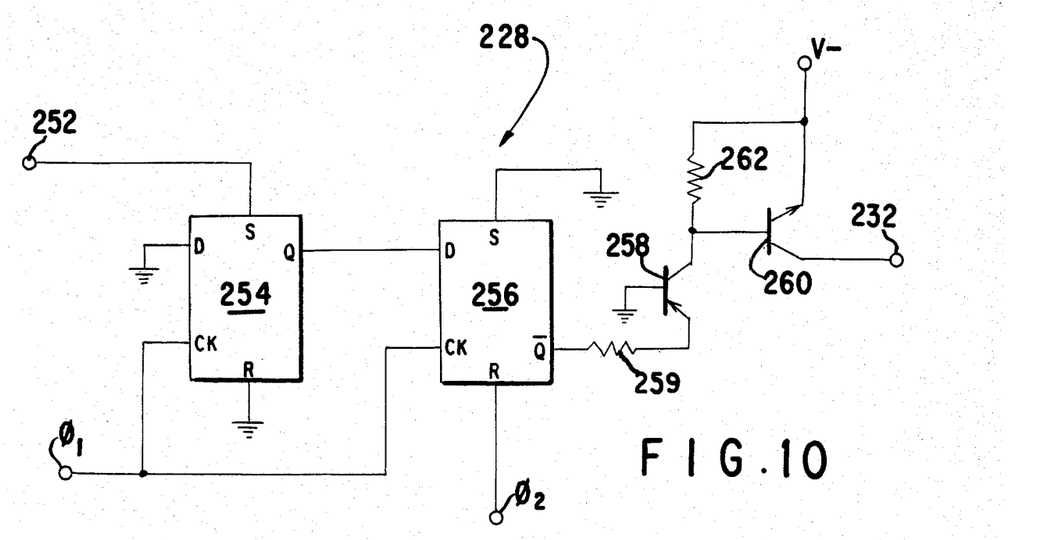
FIG. 10 is a partially block, partially schematic diagram of the pulse producing circuit of FIG. 7.

FIG. 10 is a schematic diagram of the pulse producing circuit 228 shown in block form in FIG. 7. An input terminal 252 of pulse producing circuit 228 is connected to the cathode of diode 226 to receive the positive going pulse therefrom. Terminal 252 is connected to the Set terminal of a first flip-flop 254. Flip-flop 254 has a Reset terminal connected to ground and a D terminal connected to ground. Flip-flop 254 also has a Q terminal connected to the D terminal of a second flip-flop 256. The Set terminal of flip-flop 256 is connected to ground and the $\overline{Q}$ terminal of flip-flop 256 is to the emitter of a PNP transistor 258 through a resistor 259. Resistor 259 serves to permit the voltage level at the $\overline{Q}$ terminal to rise above the voltage at the emitter of transistor 258, which is clamped at about +0.5 volts. The base of transistor 258 is connected to ground, while the collector thereof is connected to the base of an NPN transistor 260 and is coupled to a source of negative DC voltage V− through a resistor 262. The emitter of transistor 260 is connected to the source of negative DC voltage V−, while the collector of transistor 260 is connected to output terminal 232. Each of flip-flops 254 and 256 has a clock terminal connected to the $\phi_1$ terminal of pulse producing circuit 228. The Reset terminal of flip-flop 256 is connected to the $\phi_2$ terminal of pulse producing circuit 228.

In operation, a first pulse train is received at terminal $\phi_1$ and a second pulse train is received at terminal $\phi_2$. The receipt of a positive going pulse at the Set terminal of flip-flop 254 causes the Q terminal thereof to go to a 1 state. The 1 at the Q terminal of flip-flop 254 is clocked into the D terminal of flip-flop 256 upon receipt of a pulse at terminal $\phi_1$. This in turn results in a 0 state at terminal $\overline{Q}$ of flip-flop 256, thus cutting off transistor 258 and transistor 260, resulting in a low to high transition at output terminal 232, thus to provide an update pulse to the update circuit. The clock signal received at terminal $\phi_1$ also clocks the 0 level at terminal D into flip-flop 254 thus to return terminal Q to a 0 state. The subsequent receipt of a pulse at terminal $\phi_2$ will Reset flip-flop 256 causing its $\overline{Q}$ terminal to go to a 1 state, thus terminating the update pulse at terminal 232. Accordingly, the duration of the update pulse is under the control of the pulse trains provided at terminals $\phi_1$ and $\phi_2$ of pulse producing circuit 228 and is independent of the duration of the pulse received at terminal 252. The pulse producing circuit 228 is readily implemented with inexpensive components; however, circuit 228 may also be implemented with a precision monostable multivibrator.

Figure 11:
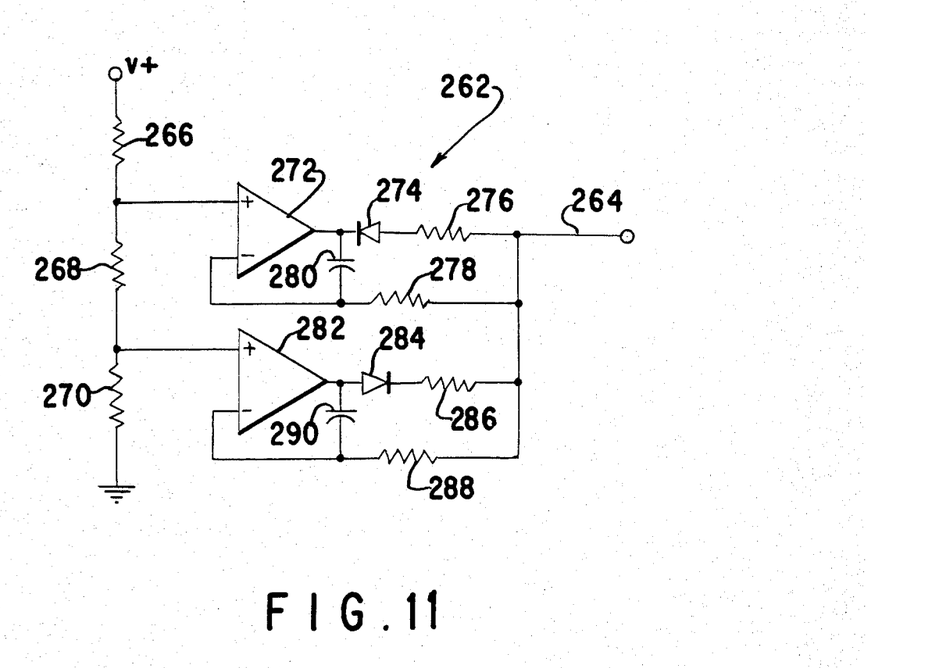
FIG. 11 is a schematic diagram of the voltage limiter of FIG. 7.

A voltage limiter 262 shown in block form in FIG. 7 limits the range of voltages that the adjustable threshold level can assume as stored in capacitor 212. FIG. 11 is a schematic diagram of the voltage limiter 262. A terminal 264 of voltage limiter 262 is connected to the first terminal of capacitor 212. A voltage divider is comprised of resistors 266, 268 and 270. A first terminal of resistor 266 is connected to a source of positive DC voltage +V and a second terminal of resistor 266 is connected to a first terminal of resistor 268. A second terminal of resistor 268 is connected to a first terminal of resistor 270 having a second terminal connected to ground. An operational amplifier 272 has its non-inverting input terminal connected to the second terminal of resistor 266 and its output terminal connected to the cathode of a diode 274. The anode of diode 274 is connected to a resistor 276 having a second terminal connected to terminal 264. A resistor 278 has a first terminal connected to terminal 264 and a second terminal connected to the inverting input terminal of amplifier 272 and a first terminal of a capacitor 280. A second terminal of capacitor 280 is connected to the output terminal of amplifier 272. An operational amplifier 282 has its non-inverting input terminal connected to the second terminal of resistor 268 and its output terminal connected to the anode of a diode 284. The cathode of diode 284 is connected to a first terminal of a resistor 286 which has a second terminal connected to terminal 264. A first terminal of a resistor 288 is connected to terminal 264 and a second terminal thereof is connected to the inverting input terminal of amplifier 282. A capacitor 290 has a first terminal connected to the second terminal of resistor 288 and a second terminal connected to the output terminal of amplifier 282.

In operation, the voltage limiter 262 prevents the adjustable voltage level stored in capacitor 212 from exceeding the voltage level established by the resistive voltage divider at the non-inverting input terminal of amplifier 272, and additionally prevents the adjustable threshold level from falling below the voltage established at the non-inverting input terminal of amplifier 282. It will be appreciated from FIG. 11 that when the voltage across capacitor 212 exceeds the voltage at the non-inverting input terminal of amplifier 272, the output thereof will be forced low causing capacitor 212 to discharge through resistor 276 and diode 274 until the voltage across capacitor 212 falls below the voltage level at the non-inverting input terminal of amplifier 272. Likewise, when the voltage across capacitor 212 falls below the voltage level at the non-inverting input terminal of amplifier 282, the output terminal thereof will be forced high so that capacitor 212 charges from the output terminal of amplifier 282 through diode 284 and resistor 286 until the voltage across capacitor 212 once again exceeds the voltage level at the non-inverting input terminal of amplifier 282. The phase-shifting effects of resistor 276 in combination with capacitor 212 and of resistor 286 in combination with capacitor 212 upon the stability of amplifiers 272 and 282, respectively, are compensated through the combination of resistor 278 and capacitor 280 and the combination of resistor 288 with capacitor 290.

The advantages of the present invention as well as certain changes and modifications of the disclosed emboidments thereof will readily apparent to those skilled in the art. It is the applicants' intention to cover by their claims all those changes and modifications which can be made to the embodiment of the invention herein chosen for the purposes of the disclosure without departing from the spirit and scope of the invention.

We claim:

1. A system for detecting the recurrence of a periodic physiological function comprising:
   an input terminal for receiving a physiological signal representing the function, the physiological signal having periodic artifact;
   threshold producing means coupled with the input terminal to receive the physiological signal for producing a minimum threshold amplitude proportional to the fundamental frequency of the periodic artifact;
   filtering means coupled with the input terminal to receive the physiological signal for suppressing the periodic artifact in the physiological signal to produce a filtered means signal therefrom; and
   threshold detecting means operable for maintaining a threshold level equal to at least the minimum threshold amplitude and for producing a recurrence signal representative of the recurrence of the physiological function in response at least in part to the filtered signal exceeding the threshold level.

2. The system of claim 1, wherein the filtering means comprises artifact producing means for producing an artifact frequency signal which varies over time with the frequency of the periodic artifact and suppressing means responsive to the artifact frequency signal for suppressing components of the physiological signal at least at the fundamental frequency of the periodic artifact.

3. The system of claim 2, wherein the suppressing means comprises time averaging filter means coupled to receive the physiological signal and with the artifact producing means to receive the artifact frequency signal, for filtering the physiological signal in accordance with the relationship:

$$v_f(t) = \int_0^T v_{ph}(t)dt,$$

wherein $v_f(t)$ represents the filtered signal as it varies with time, t; $v_{ph}(t)$ represents the physiological signal as it varies with time, t; and the interval 0 to T is variable under the control of the artifact frequency signal to substantially equal the period of the fundamental frequency of the periodic artifact.

4. The system of claim 2, wherein the suppressing means comprises band-reject filter means operable for suppressing components of the physiological signal having a frequency equal to the fundamental frequency of the periodic artifact; and low pass filter means cascaded with the band-reject filter means operable for suppressing components of the physiological signal having a frequency at least equal to the second harmonic frequency of the periodic artifact.

5. The system of claim 2, wherein the suppressing means comprises a variable delay line having an input coupled to receive the physiological signal and having a succession of taps, each providing the physiological signal delayed by successively greater time intervals; wherein the longest time interval varies with the artifact frequency signal such that it is equal to the period of the fundamental frequency component of the periodic artifact; and summing means having a plurality of summing terminals each coupled with a respective one of the taps for summing the delayed physiological signals to produce the filtered means signal.

6. The system of claim 2, wherein the suppressing means comprises a low pass filter, a high pass filter, and means for summing the output signals of the low pass filter and the high pass filter to provide the filtered means signal, the low pass filter and the high pass filter being coupled to receive the physiological signal and operative to pass low frequency components and high frequency components, respectively, of the physiological signal; the low pass filter and the high pass filter having respective low pass means and high pass means operable in response to the artifact frequency signal for attenuating components of the physiological signal at the artifact frequency in the filtered means signal; the high pass means further operable in response to the artifact frequency signal for controlling the gain of the high pass filter such that the value of the gain of the high pass filter is lower than the gain of the low pass filter whereby components of the physiological signal having frequencies in the range of the harmonic frequencies of the artifact frequency are suppressed in the filtered means signal relative to components of the physiological signal having frequencies below the artifact frequency.

7. The system of claim 1, wherein the filtering means comprises artifact producing means for producing an artifact signal proportional to the periodic artifact in the physiological signal; and wherein the threshold producing means comprises envelope detector means coupled to the artifact producing means to receive the artifact signal for producing an output signal whose level serves as the minimum threshold amplitude.

8. The system of claim 7, wherein the artifact producing means comprises bandpass means which includes an output terminal and which is coupled to the input terminal to receive the physiological signal for suppressing those components of the physiological signal outside a pass band including the fundamental frequency of the periodic artifact and providing the filtered physiological signal as the artifact signal to the output terminal which is coupled to the envelope detector means.

9. The system of claim 8, wherein the bandpass means comprises tachometer means for producing an artifact frequency voltage which varies over time in accordance with the fundamental frequency of the periodic artifact and a bandpass filter coupled to the input terminal to receive the physiological signal and coupled with the output terminal of the bandpass means to provide the artifact signal thereto; the bandpass filter having a pass band and means for varying the pass band in accordance with the artifact frequency voltage.

10. The system of claim 9, wherein the bandpass filter comprises means operable for inducing a phase shift substantially equal to 180 degrees in the artifact signal; and wherein the filtering means further comprises summing means having a first summing terminal coupled with the input terminal to receive the physiological signal and a second summing terminal coupled to the output terminal of the bandpass means to receive the artifact signal for summing the physiological signal and the artifact signal to yield a sum signal, and low pass means having an input coupled with the summing means to receive the sum signal for filtering the sum signal by suppressing those components of the sum signal having frequencies at least equal to the second harmonic frequency of the periodic artifact and coupled with the threshold detecting means for providing the filtered sum signal thereto as the filtered means signal.

11. A system for detecting the recurrence of a physiological function comprising:
an input terminal for receiving an unfiltered physiological signal representing the function, the unfiltered physiogical signal having periodic artifact;
means coupled with the input terminal to receive the unfiltered physiological signal, for producing a threshold level from the unfiltered physiological signal;
filtering means coupled with the input terminal to receive the unfiltered physiological signal for suppressing the periodic artifact in the unfiltered physiological signal to produce a filtered signal therefrom; and
threshold crossing detecting means for producing a recurrence signal representative of the recurrence of the physiological function in response at least in part to the filtered signal crossing the threshold level.

12. The system of claim 11, wherein the means for producing the threshold level comprises:
storage means for storing the threshold level;
comparing means for comparing the threshold level against a signal level proportional to at least a portion of the unfiltered physiological signal to provide an update signal in response to a deviation of the threshold level from the proportional signal level toward a predetermined polarity; and
updating means for modifying the threshold level in response to the update signal to oppose the deviation of the threshold level from the proportional signal level.

13. The system of claim 12, wherein the updating means comprises means operable for modifying the threshold level to a value proportional to the threshold level prior to the modification.

* * * * *